United States Patent
Poole et al.

(10) Patent No.: US 9,028,462 B2
(45) Date of Patent: May 12, 2015

(54) DISPOSABLE ABSORBENT GARMENT HAVING COLORED FACINGS AND INTEGRAL WAISTBAND

(71) Applicant: Kimberly-Clark Worldwide, Inc., Neenah, WI (US)

(72) Inventors: Lacey L. Poole, Appleton, WI (US); Marleen R. Dins, Appleton, WI (US); Marie E. Boll, Appleton, WI (US); Julie Ann Paveletzke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 28 days.

(21) Appl. No.: 14/087,582

(22) Filed: Nov. 22, 2013

(65) Prior Publication Data

US 2014/0155857 A1 Jun. 5, 2014

Related U.S. Application Data

(62) Division of application No. 13/161,160, filed on Jun. 15, 2011, now abandoned.

(51) Int. Cl.
*A61F 13/49* (2006.01)
*A61F 13/496* (2006.01)
*A61F 13/515* (2006.01)
*A61F 13/84* (2006.01)

(52) U.S. Cl.
CPC ..... *A61F 13/49014* (2013.01); *A61F 13/49012* (2013.01); *A61F 13/49011* (2013.01); *A61F 13/515* (2013.01); *A61F 2013/8497* (2013.01); *A61F 13/496* (2013.01)

(58) Field of Classification Search
CPC .............. A61F 13/49007; A61F 13/49009; A61F 13/49011; A61F 13/49012; A61F 13/49019; A61F 13/4902; A61F 13/51478; A61F 2013/49022; A61F 2013/49025; A61F 13/49031; A61F 13/49038
USPC ............ 604/385.24, 385.29, 385.3, 394, 396
See application file for complete search history.

(56) References Cited

U.S. PATENT DOCUMENTS

| | | | |
|---|---|---|---|
| 5,019,066 A | 5/1991 | Freeland et al. | |
| 5,561,860 A | 10/1996 | Nguyen-senderowicz | |
| 5,601,547 A | 2/1997 | Kato et al. | |
| 5,612,118 A | 3/1997 | Schleinz et al. | |
| 5,675,842 A | 10/1997 | Schaefer | |
| 5,690,627 A | 11/1997 | Clear et al. | |
| 6,083,212 A * | 7/2000 | Kumasaka | 604/385.29 |

(Continued)

FOREIGN PATENT DOCUMENTS

EP 1 537 842 A1 6/2005
WO WO 2007/024327 A1 3/2007

*Primary Examiner* — Tan-Uyen (Jackie) T Ho
*Assistant Examiner* — Kathryn E Ditmer
(74) *Attorney, Agent, or Firm* — Kimberly-Clark Worldwide, Inc.

(57) ABSTRACT

A garment comprises a laminate. The laminate comprises a first layer colored a first color, and a second layer colored a second color different than the first color. The laminate includes a folded flap in the waist region, thereby defining an integral, outwardly visible waistband having a waistband lower edge. The first layer and the second layer are coterminous at the waistband lower edge and the folded flap is an outwardly folded flap. The first layer is an inner layer and the second layer is an outer layer, and the outwardly visible waistband is colored the first color. The distinction between the first color and second color in conjunction with the fold creates a visible waistband effect.

8 Claims, 4 Drawing Sheets

(56) References Cited

U.S. PATENT DOCUMENTS

| | | |
|---|---|---|
| 6,138,282 A | 10/2000 | Follese |
| 6,210,386 B1* | 4/2001 | Inoue .................. 604/385.13 |
| 6,306,122 B1* | 10/2001 | Narawa et al. ............ 604/385.3 |
| 6,336,921 B1* | 1/2002 | Kato et al. ............... 604/385.3 |
| 7,896,858 B2 | 3/2011 | Trennepohl et al. |
| 2005/0027274 A1 | 2/2005 | Suzuki et al. |
| 2005/0126689 A1* | 6/2005 | Thorson et al. ............. 156/164 |
| 2006/0047260 A1* | 3/2006 | Ashton et al. ............. 604/396 |
| 2007/0088312 A1* | 4/2007 | Langdon et al. ............. 604/396 |
| 2007/0282292 A1* | 12/2007 | Harkness .................. 604/396 |
| 2008/0009817 A1* | 1/2008 | Norrby ..................... 604/385.3 |
| 2008/0134487 A1* | 6/2008 | Hartono ....................... 29/428 |

\* cited by examiner

DISPOSABLE ABSORBENT GARMENT HAVING COLORED FACINGS AND INTEGRAL WAISTBAND

PRIORITY

This application is a divisional of prior application Ser. No. 13/161,160 entitled Disposable Absorbent Garment Having Colored Facings and Integral Waistband and filed in the U.S. Patent and Trademark Office on Jun. 15, 2011, now abandoned. The entirety of the prior application is hereby incorporated by reference in this application.

BACKGROUND OF THE INVENTION

Pant-like disposable absorbent garments are in common use in today's society. For example, disposable absorbent underwear for incontinence and enuresis conditions, disposable training pants, and disposable menstrual panties are common in the marketplace. It is desirable to make such products as much like normal cloth underwear as possible. For example, wearers of incontinence and enuresis garments generally wish to conceal the fact that they are wearing such products, and therefore desire the garments to resemble normal cloth underwear as closely as possible. In another example, children wearing training pants take pride in the fact that they are no longer wearing diapers, and providing them with a disposable training pant product that closely resembles real underwear supports this process. It is also important that such garments provide a snug and secure fit, both to provide comfort to the wearer and to minimize leakage of bodily waste out of the absorbent garment.

For example, it is common for many products to include waistbands or leg bands, often elasticized, to provide improved fit, leakage management, and underwear-like aesthetics. In one conventional approach, the waist edge of a disposable absorbent garment is folded over. However, in such conventional products, the folded edge region is the same color as the remainder of the waist region; as a result, the folded waistband is generally not visible to a viewer, because the folded waistband "blends in" with the color of the underlying material. In another approach, a waistband graphic is printed onto the garment in the vicinity of the waist opening to resemble a separately attached waistband. However, such an approach can introduce undesirably process complexity, equipment cost, and ink expense. In still another conventional approach, a separate waistband material is provided and attached to the garment. While this approach can provide a more garment-like look in many instances, it introduces additional process complexity and expense, and introduces additional cost associated with raw material procurement and inventory.

Therefore, there remains a need for pant-like disposable garments that better resemble normal cloth underwear.

SUMMARY OF THE INVENTION

In response to aforementioned need, an improved disposable absorbent garment having an integral waistband has been invented.

In one embodiment, the garment comprises a laminate. The laminate comprises a first layer colored a first color, and a second layer colored a second color different than the first color. The laminate includes a folded flap in the waist region, thereby defining an integral, outwardly visible waistband having a waistband lower edge. The first layer and the second layer are coterminous at the waistband lower edge.

In another embodiment, the garment defines a longitudinal direction and a transverse direction, and includes a front waist panel, a back waist panel, and a crotch panel interconnecting the front waist panel and the back waist panel. The front waist panel is attached to the back waist panel along a pair of transversely opposed side seams to define a waist opening and two leg openings. The front waist panel and the back waist panel each comprise a laminate. The laminate comprises an inner layer colored a first color, and an outer layer colored a second color different than the first color. The laminate includes an outwardly folded flap proximate the waist opening, thereby defining an integral, outwardly visible waistband having a waistband lower edge. The inner layer and the outer layer are coterminous at the waistband lower edge. The outwardly visible waistband is colored the first color.

In another embodiment, the garment defines a longitudinal direction and a transverse direction, and includes a front waist panel, a back waist panel, and a crotch panel interconnecting the front waist panel and the back waist panel. The front waist panel is attached to the back waist panel along a pair of transversely opposed side seams to define a waist opening and two leg openings. The front waist panel and the back waist panel each comprise a laminate. The laminate comprises an inner layer colored a first color, and an outer layer colored a second color different than the first color. The laminate is folded upon itself proximate the waist opening, thereby defining an integral, outwardly visible waistband having a waistband lower edge. The inner layer and the outer layer are coterminous at the waistband lower edge. The outwardly visible waistband is colored the first color.

In still another embodiment, the garment defines a longitudinal direction and a transverse direction, and comprises a front waist panel, a back waist panel, and a crotch panel interconnecting the front waist panel and the back waist panel. The front waist panel is attached to the back waist panel along a pair of transversely opposed side seams to define a waist opening and two leg openings. The front waist panel and the back waist panel each comprise a laminate. Each laminate comprises first, inner layer colored a first color, and a second, outer layer colored a second color different than the first color. The second layer defines an outer surface and an inner surface. The first layer includes an outwardly folded flap proximate the waist opening so as to define an integral, outwardly visible waistband having a waistband lower edge. The outwardly visible waistband is colored the first color.

BRIEF DESCRIPTION OF THE DRAWINGS

FIG. 3A is a cross-sectional view of the article of FIG. 3 as viewed along line 3A-3A.

DETAILED DESCRIPTION OF PARTICULAR EMBODIMENTS

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

A description of exemplary embodiments of the garment of the present invention shall now be presented. Examples of the pant-like disposable absorbent garment are adult incontinence absorbent underwear, youth absorbent enuresis pants, children's absorbent training pants, absorbent menstrual panties, and the like.

Figure 1:
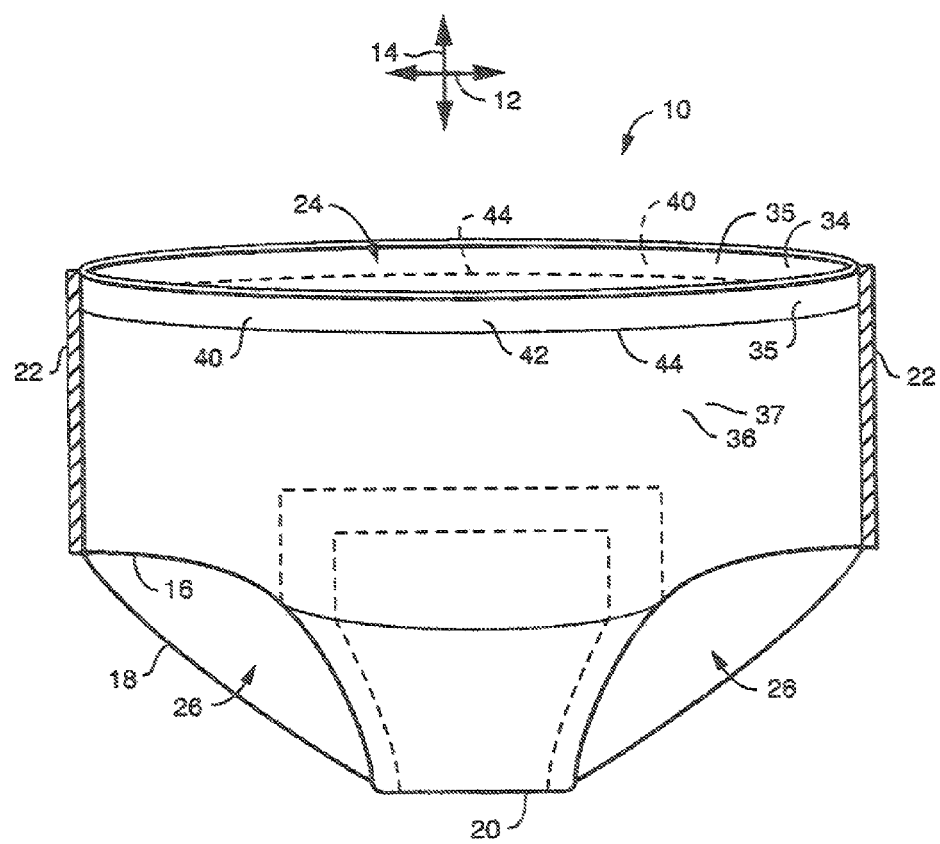
FIG. 1 representatively illustrates a front perspective view of a disposable absorbent garment incorporating principles of the garment of the present invention.
Figure 2:
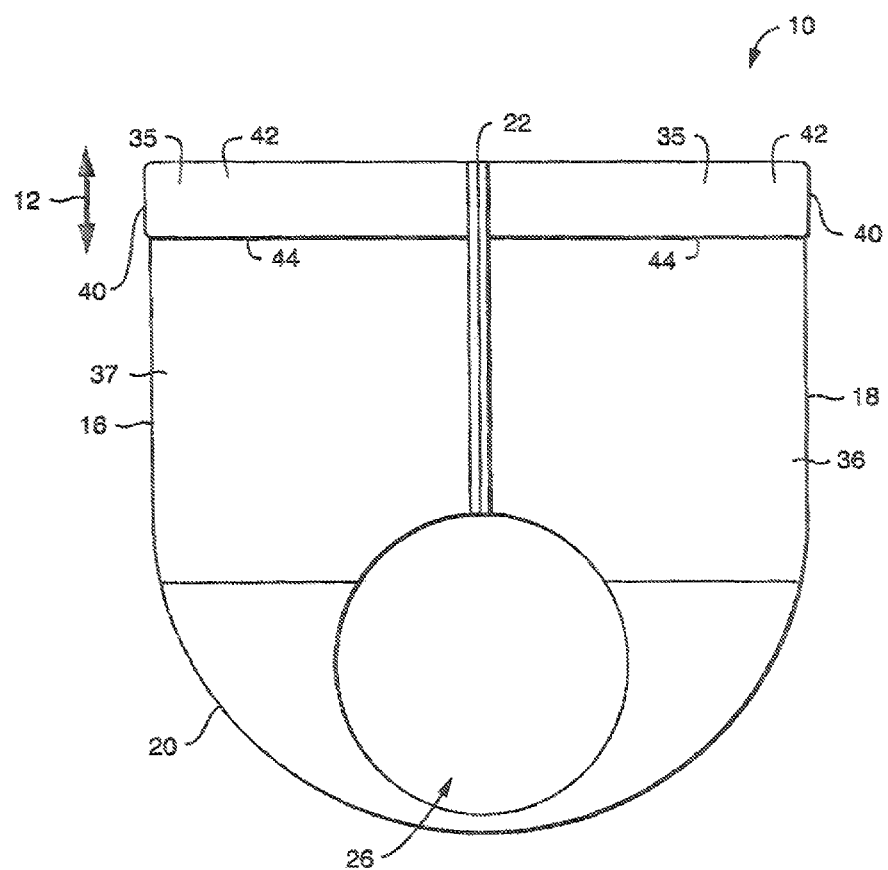
FIG. 2 is a side view of the garment of FIG. 1.
Figure 3:
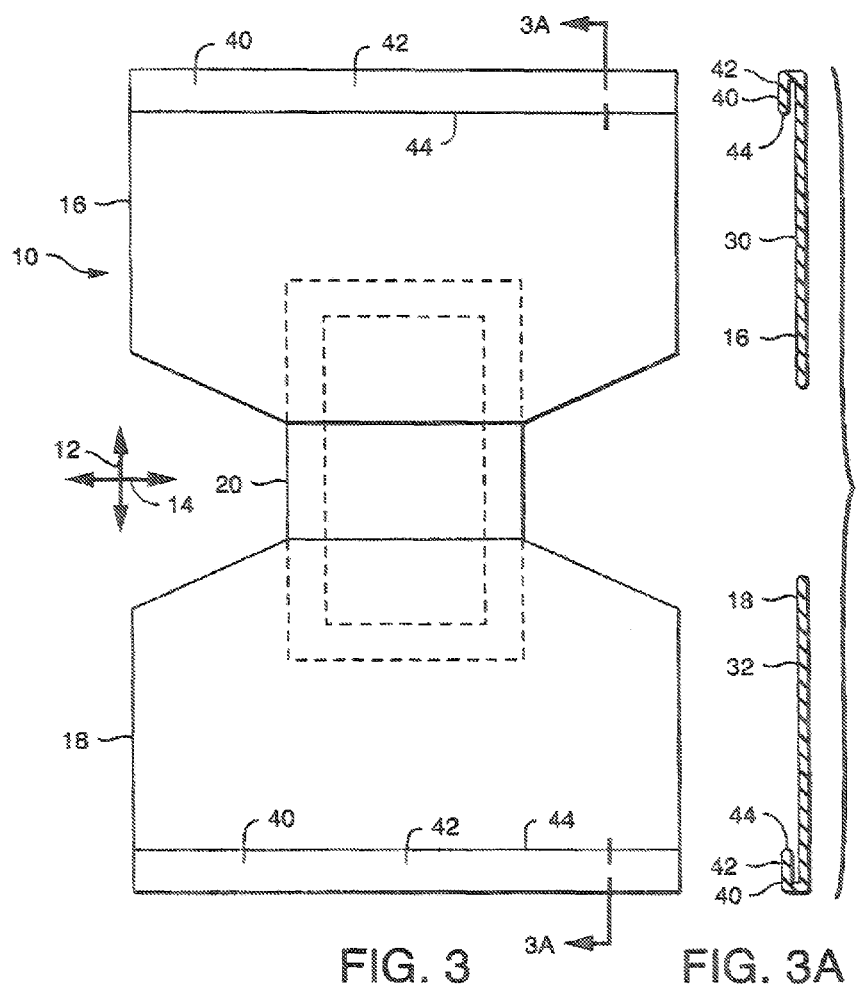
FIG. 3 is a plan view of the garment of FIG. 1, shown in a laid-flat condition, prior to the joining of the front and back waist regions, and showing the surface of the article that faces away from the wearer when the article is worn.

Referring to FIGS. 1-3, the invention in particular embodiments is directed to a pant-like disposable absorbent garment 10 that defines a longitudinal direction 12 and a transverse direction 14. The garment 10 includes a front waist panel 16, a back waist panel 18, and a crotch panel 20 interconnecting the front waist panel 16 and the back waist panel 18. The front waist panel 16, the back waist panel 18, and the crotch panel 20 can be separate, distinct panels that are attached to each other. Alternatively, the front waist panel 16, the back waist panel 18, and the crotch panel 20 can be integral with each other. The front waist panel 16 is attached to the back waist panel 18 along a pair of transversely opposed side seams 22 to define a waist opening 24 and two leg openings 26. The side seams 22 can be refastenable or non-refastenable.

The front waist panel 16 is formed from a laminate 30, and the back waist panel 18 is formed from a laminate 32. The laminate 30 of the front waist panel 16 and the laminate 32 of the back waist panel 18 each include a first layer 34 colored a first color 35. Each laminate 30, 32 further includes a second layer 36 colored a second color 37 different than the first color. As used herein, "colored" means having a particular color or pattern over substantially the entire area of the layer, such as, for example, by virtue of being dyed, pigmented, printed, or the like. Examples of "colored" include but are not limited to: being dyed beige; being dyed gray; being printed with stripes; not being dyed or printed but instead being naturally and inherently white, gray, or another color; and the like. Preferably, the first layer 34 is predominantly the inner, bodyside layer, and the second layer 36 is predominantly the outer, non-bodyside layer, though in particular embodiments this could be reversed. In particular embodiments, the first color 35 is not white, and the second color 37 is white. In other embodiments, the first color 35 is white, and the second color 37 is not white. In still other embodiments, both the first color 35 and the second color 37 are not white.

At least one of the laminate of the front waist panel 16 and the laminate of the back waist panel 18, and preferably both laminates, includes a folded flap 40 proximate the waist opening 24. The folded flap 40 defines an integral, outwardly visible waistband 42. In particular embodiments, the folded flap 40 is an outwardly folded flap 40. In particular embodiments, the laminate 30, 32 is folded upon itself proximate the waist opening 24, thereby defining an integral, outwardly visible waistband 42. "Outwardly folded" means folded in a direction away from the wearer of the garment. In other embodiments, the folded flap 40 is an inwardly folded flap. "Inwardly folded" means folded in a direction toward the wearer of the garment. "Outwardly visible" means visible from the non-bodyside surface of the garment when the garment is donned.

Figure 4:
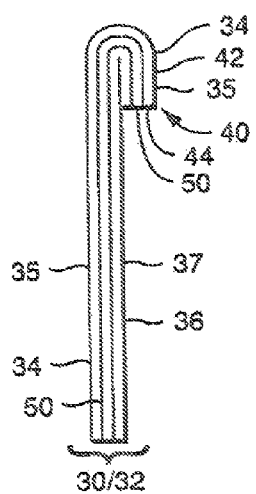
FIG. 4 is a detailed cross-sectional view of a waist panel of one embodiment of the garment of the present invention.

The waistband 42 defines a waistband lower edge 44. In particular embodiments, such as those representatively illustrated in FIGS. 4-6, the inner layer 34 and the outer layer 36 are coterminous at the waistband lower edge 44. The outwardly visible waistband 42 is colored the first color 35. In this manner, in particular embodiments, a more garment-like appearance can be achieved in disposable absorbent garments with reduced complexity and cost.

Figure 5:
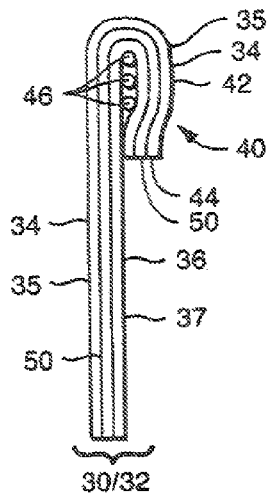
FIG. 5 is a detailed cross-sectional view of a waist panel of another embodiment of the garment of the present invention.
Figure 6:
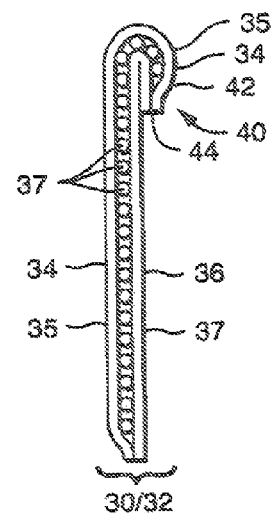
FIG. 6 is a detailed cross-sectional view of a waist panel of yet another embodiment of the garment of the present invention.

In particular embodiments, such as that representatively illustrated in FIG. 5, one or more elastic strands or strips 46 are sandwiched between the flap 40 and the remainder of the laminate 30 in the front waist panel 16. Additionally or alternatively, one or more elastic strands 46 are sandwiched between the flap 40 and the remainder of the laminate 32 in the back waist panel 18. Desirably, the elastic strands 46 impart retractive forces to the laminate 30/32 to create a "gathered" waistband.

In particular embodiments, both the first layer 34 and the second layer 36 comprise nonwoven polyolefin-based material, and each laminate 30, 32 comprises an elastomeric film layer 50 sandwiched between the first layer 34 and the second layer 36. In such embodiments, it is preferable that the elastomeric film layer 50 be coterminous with both the first layer 34 and the second layer 36 around the entire periphery of the laminate 30, 32. The elastomeric film layer 50 can itself be clear, translucent, or opaque, and can be colored white or can be colored a non-white color.

Figure 7:
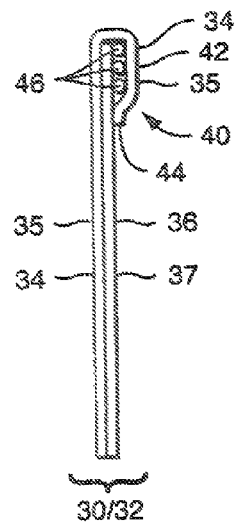
FIG. 7 is a detailed cross-sectional view of a waist panel of still another embodiment of the garment of the present invention.
Figure 8:
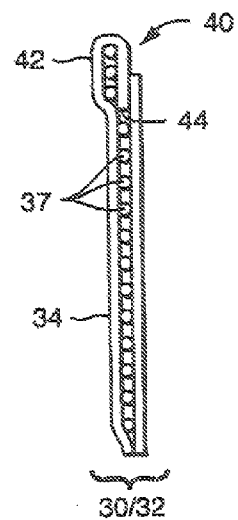
FIG. 8 is a detailed cross-sectional view of a waist panel of still another embodiment of the garment of the present invention.

Referring to FIGS. 7 and 8, in alternative embodiments, the laminate of the 30 of the front waist panel 16 and/or the laminate 32 of the back waist panel 18 include a first layer 34 colored a first color 35, and further include a second layer 36 colored a second color 37 different than the first color 35. The second layer 36 defines an outer surface 38 and an inner surface 39. The outer surface 38 faces away from the center of the laminate sandwich, while the inner surface 39 faces toward the center of the laminate sandwich. The first layer 34 includes a folded flap 40 proximate the waist opening 24 so as to define an integral, outwardly visible waistband 42 having a waistband lower edge 44. In particular embodiments, the flap 40 is bonded to the outer surface 38 of the second layer 36 so as to define an integral, outwardly visible waistband 42 having a waistband lower edge 44.

In the exemplary embodiment of FIG. 7, the folded flap 40 is an outwardly folded flap. The first layer 34 is an inner, bodyside layer, and the second layer 36 is an outer, non-bodyside layer, and the outwardly visible waistband 42 is colored the first color 35. In such an embodiment, the outwardly visible waistband 42 is colored the first color 35 because the first layer 34 is colored the first color and is outwardly folded to cover the second layer 36 proximate the waist opening 24.

In the exemplary embodiment of FIG. 8, the folded flap 40 is an inwardly folded flap. The first layer 34 is an outer, non-bodyside layer colored a first color 35, and the second layer 36 is an inner, bodyside layer colored a second color 37, and the outwardly visible waistband 42 is colored the first color 35. In such an embodiment, although the entire outer layer 34 is colored the same first color, the integral waistband 42 is nonetheless outwardly visible, because in such an embodiment the first (outer) layer 34 is translucent. When viewed from the outside (that is, from the non-bodyside surface of the garment when the garment is donned), the translucent outer layer 34 is underlain by the folded flap 40 (which is colored the first color 35) proximate the waist opening. In contrast, when viewed from the outside, the translucent outer layer 34 is underlain by the second (inner) layer 36 (which is colored the second color 37). As a result, though the folded flap 40 is positioned on the inside (that is, the bodyside) of the garment, an outwardly visible, integral waistband 42 can be created due to the contrast created by the differently colored underlying materials. In certain embodiments, in which the flap 40 contacts or overlaps the second (inner) layer 36, the waistband lower edge 44 is outwardly visible through the translucent first (outer) layer 34. This configuration is representatively illustrated in FIG. 8.

In particular embodiments, such as that representatively illustrated in FIG. 7, one or more elastic strands or strips 46 are sandwiched between the flap 40 and the remainder of the laminate 30 in the front waist panel 16. Additionally or alternatively, one or more elastic strands 46 are sandwiched between the flap 40 and the remainder of the laminate 32 in the back waist panel 18. In particular embodiments, at least one elastic strand 46 is sandwiched between the flap 40 and the second layer 36 in the front waist panel, and at least one elastic strand 46 is sandwiched between the flap 40 and the second layer 36 in the back waist panel. Desirably, the elastic strands 46 impart retractive forces to the laminate 30/32 to create a "gathered" waistband. In an alternative embodiment (not shown), one or more elastic strands 46 are sandwiched within the fold 40 of the first layer 34 without overlapping or contacting the second layer 36. In particular embodiments, as is representatively illustrated in FIGS. 6 and 8, elastomeric materials, such as elastomeric strands 47, can be sandwiched between the first layer 34 and the second layer 36, thereby constituting a part of the laminate 30, 32.

In particular embodiments, the first color 35 is not white, and the second color 37 is white. In other embodiments, the opposite is true. In still other embodiments, both the first and second colors 35, 37 are not white.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A pant-like disposable absorbent garment defining a longitudinal direction and a transverse direction, the garment comprising a front waist panel, a back waist panel, and a crotch panel interconnecting the front waist panel and the back waist panel, the front waist panel being attached to the back waist panel along a pair of transversely opposed side seams to define a waist opening and two leg openings, the front waist panel and the back waist panel each comprising a laminate, each laminate comprising:
    an inner layer comprising nonwoven polyolefin-based material and colored a first color;
    an outer layer comprising nonwoven polyolefin-based material and colored a second color different than the first color;
    an elastomeric film layer sandwiched between the inner layer and the outer layer, the elastomeric film layer being coterminous with both the inner layer and the outer layer around a periphery of the laminate;
    wherein each laminate includes an outwardly folded flap proximate the waist opening, thereby defining an integral, outwardly visible waistband having a waistband lower edge,
    wherein at least one elastic strand is sandwiched between the outwardly folded flap and the remainder of the laminate in the front waist panel, and wherein at least one elastic strand is sandwiched between the outwardly folded flap and the remainder of the laminate in the back waist panel, and
    wherein the inner layer and the outer layer are coterminous at the waistband lower edge and the outwardly visible waistband is colored the first color.

2. The disposable absorbent garment of claim 1, wherein the first color is not white, and the second color is white.

3. The disposable absorbent garment of claim 1, wherein the elastomeric film layer is colored a non-white color.

4. The disposable absorbent garment of claim 1, wherein more than one elastic strand is sandwiched between the outwardly folded flap and the remainder of the laminate in the front waist panel to impart retractive forces and create a gathered waistband and wherein more than one elastic strand is sandwiched between the outwardly folded flap and the remainder of the laminate in the back waist panel to impart retractive forces and create a gathered waistband.

5. A pant-like disposable absorbent garment defining a longitudinal direction and a transverse direction, the garment comprising a front waist panel, a back waist panel, and a crotch panel interconnecting the front waist panel and the back waist panel, the front waist panel being attached to the back waist panel along a pair of transversely opposed side seams to define a waist opening and two leg openings, the front waist panel and the back waist panel each comprising a laminate, each laminate comprising:
    an inner layer colored a first color and comprising nonwoven polyolefin-based material;
    an outer layer colored a second color different than the first color and comprising nonwoven polyolefin-based material;
    an elastomeric film layer sandwiched between the inner layer and the outer layer, the elastomeric film layer being coterminous with both the inner layer and the outer layer around a periphery of the laminate wherein each laminate includes an outwardly folded flap folded upon itself proximate the waist opening, thereby defining an integral, outwardly visible waistband having a waistband lower edge, the inner layer and the outer layer being coterminous at the waistband lower edge, the outwardly visible waistband colored the first color and having at least one elastic strand sandwiched between the flap and the remainder of the laminate in the front waist panel and having at least one elastic strand sandwiched between the flap and the remainder of the laminate in the back waist panel.

6. The disposable absorbent garment of claim 5, wherein the first color is not white, and the second color is white.

7. The disposable absorbent garment of claim 5, wherein the elastomeric film layer is colored a non-white color.

8. The disposable absorbent garment of claim 5, wherein more than one elastic strand is sandwiched between the outwardly folded flap and the remainder of the laminate in the front waist panel to impart retractive forces and create a gathered waistband and wherein more than one elastic strand is sandwiched between the outwardly folded flap and the remainder of the laminate in the back waist panel to impart retractive forces and create a gathered waistband.

* * * * *